(12) United States Patent
Boles et al.

(10) Patent No.: US 9,012,373 B2
(45) Date of Patent: Apr. 21, 2015

(54) SYSTEMS AND METHODS FOR PROCESSING FLUIDS

(75) Inventors: T. Christian Boles, Bedford, MA (US); Ezra Solomon Abrams, Newton, MA (US)

(73) Assignee: Sage Science, Inc., Beverly, MA (US)

( * ) Notice: Subject to any disclaimer, the term of this patent is extended or adjusted under 35 U.S.C. 154(b) by 0 days.

(21) Appl. No.: 13/566,806

(22) Filed: Aug. 3, 2012

(65) Prior Publication Data
US 2013/0079251 A1 Mar. 28, 2013

Related U.S. Application Data

(60) Provisional application No. 61/515,063, filed on Aug. 4, 2011.

(51) Int. Cl.
| | |
|---|---|
| B01L 3/00 | (2006.01) |
| C12N 15/10 | (2006.01) |
| C40B 50/06 | (2006.01) |
| C12M 1/00 | (2006.01) |
| C12P 19/34 | (2006.01) |

(52) U.S. Cl.
CPC ....... *C12N 15/1003* (2013.01); *B01L 3/502715* (2013.01); *B01L 3/502776* (2013.01); *C12N 15/102* (2013.01); *C40B 50/06* (2013.01); *C12M 45/09* (2013.01); *C12P 19/34* (2013.01); *B01L 3/502753* (2013.01); *B01L 3/502761* (2013.01); *B01L 2400/086* (2013.01); *B01L 2200/0652* (2013.01); *B01L 2300/0819* (2013.01)

(58) Field of Classification Search
None
See application file for complete search history.

(56) References Cited

U.S. PATENT DOCUMENTS

| | | | |
|---|---|---|---|
| 4,835,263 | A | 5/1989 | Nguyen et al. |
| 5,801,115 | A | 9/1998 | Albers et al. |
| 7,150,812 | B2 | 12/2006 | Huang et al. |
| 7,735,652 | B2 | 6/2010 | Inglis et al. |
| 7,988,840 | B2 | 8/2011 | Huang et al. |
| 2006/0223178 | A1* | 10/2006 | Barber et al. ................. 435/325 |
| 2010/0059414 | A1 | 3/2010 | Sturm et al. |

FOREIGN PATENT DOCUMENTS

| | | |
|---|---|---|
| WO | WO-9604000 A1 | 2/1996 |
| WO | WO-2003087370 A1 | 10/2003 |
| WO | WO-2006108101 A2 | 10/2006 |
| WO | WO-2008016414 A2 | 2/2008 |
| WO | WO-2010048605 A1 | 4/2010 |

OTHER PUBLICATIONS

Boom et al. "Rapid and Simple Method for Purification of Nucleic Acids." *J. Clin. Microbiol.* 28.3(1990):495-503.
Chiu et al. "Differential Dependence on Chromatin Structure for Copper and Iron Ion Induction of DNA Double-Strand Breaks." *Biochem.* 34(1995):2653-2661.
Ciulla et al. "A Simpe Method for DNA Purification from Peripheral Blood." *Anal. Biochem.* 174(1988):485-488.
Davis et al. "Deterministic Hydrodynamicics: Taking Blood Apart." *PNAS.* 103.40(2006):14779-14784.
Diehl et al. "BEAMing: Single-Molecule PCR on Microparticles in Water-in-Oil Emulsions." *Nat. Methods.* 3.7(2006):551-559.
Goryshin et al. "Tn5 in vitro Transposition." *J. Biol. Chem.* 273. 13(1998):7367-7374.
Green et al. "Charting a Course for Genomic Medicine from Base Pairs to Bedside." *Nature.* 470(2011):204-213.
Griffin et al. "In vitro Transposition of Tn552: A Tool for DNA Sequencing and Mutagenesis." *Nucleic Acids Res.* 27.19(1999):3859-3865.
Huang et al. "Continuous Particle Separation Through Deterministic Lateral Displacement." *Science.* 304(2004):987-990.
Inglis et al. "Critical Particle Size for Fractionation by Deterministic Lateral Displacement." *Lab on a Chip.* 6(2006):655-658.
Kumar et al. "Pyrrolidine Nucleic Acids: DNA/PNA Oligomers with 2-Hydroxy/Aminomethyl-4-(thymin-1-yl)pyrrolidine-$N$-acetic Acid." *Org. Lett.* 3.9(2001):1269-1272.
Kunkel et al. "Analysis of Human Y-Chromosome-Specific Reiterated DNA in Chromosome Variants." *PNAS.* 74.3(1977):1245-1249.
Lagriffoul et al. "The Synthesis, Co-Oligomerization and Hybridization of a Thymine-Thymine Heterodimer Containing PNA." *Bioorg. Med. Chem. Lett.* 4.8(1994):1081-1082.
Margulies et al. "Genome Sequencing in Microfabricated High-Density Picolitre Reactors." *Nature.* 437.7057(2005):376-380.
Morton et al. "Crossing Microfluidic Streamlines to Lyse, Label and Wash Cells." *Lab on a Chip.* 8.9(2008):1448-1453.
Petersen et al. "Synthesis and Oligomerization of $N5$-Boc-$N\alpha$-(thymin-1-ylacetyl)ornithine." *Bioorg. Med. Chem. Lett.* 6.7(1996):793-796.
Riehn et al. "Restriction Mapping in Nanofluidic Devices." *PNAS.* 102(2005):10012-10016.
Robertson et al. "Diffusion of Isolated DNA Molecules: Dependence on Length and Topology." *PNAS.* 103.19(2006):7310-7314.
Rothberg et al. "An Integrated Semiconductor Device Enabling Non-Optical Genome Sequencing." *Nature.* 475.7356(2011):348-352.
Smith et al. "A Physical Map of the *Escherichia coli*K12 Genome." *Science.* 236.4807(1987):1448-1453.
Worcel et al. "On the Structure of the Folded Chromosome of *Escherichia coli*." *J. Mol. Biol.* 71.2(1972):127-147.
Zaret et al. "Micrococcal Nuclease Analysis of Chromatin Structure." *Curr. Protoc. Mol. Biol.* S69(2005):21.1.1-21.1.17.

* cited by examiner

*Primary Examiner* — Tracy Vivlemore
*Assistant Examiner* — Karen S Weiler
(74) *Attorney, Agent, or Firm* — Cooley LLP; Brian P. Hopkins

(57) ABSTRACT

Systems and methods for processing fluid samples are disclosed. Fluid sample processing is accomplished using a series of microfluidic bump arrays include an automated and integrated system for sorting particles from a biological sample, lysing those particles to expose total RNA or DNA, purifying the RNA or DNA, processing the RNA or DNA by chemical or enzymatic modification, to select RNA or DNA molecules by size, or to generate, optionally, a sequencing library. The sequencing library is suitable for use in next generation sequencing ("NGS").

15 Claims, 10 Drawing Sheets

SYSTEMS AND METHODS FOR PROCESSING FLUIDS

CROSS-REFERENCE TO RELATED APPLICATION

The present application claims priority to U.S. Provisional Patent Application No. 61/515,063 to Boles, filed Aug. 4, 2011, and entitled "Microfluidic Bump Array," and incorporates its disclosure herein by reference in its entirety.

TECHNICAL FIELD

The present disclosure relates generally to the field of molecular biology, and in particular to systems and methods that can be used to isolate high molecular weight Ribonucleic Acid ("RNA") and Deoxyribonucleic Acid ("DNA") from biological samples, wherein the RNA and DNA molecules can be subsequently sorted by size and/or used to generate sequencing libraries.

BACKGROUND

Next-generation sequencing ("NGS") has revolutionized research in many areas of molecular biology, genetics, and medicine. As NGS technology has become more affordable and more widely available over the past few years, there has been increasing focus on the need for more efficient and reproducible sample preparation methods for NGS library generation. Conventional methods involve many cycles of enzymatic modification followed by purification, an arrangement that is laborious, time-consuming, and prone to template loss.

Conventional processing and purification methods in molecular biology involve nucleic acids undergoing sequential cycles of treatment followed by purification, wherein treatment and purifications are usually carried out in a separate tubes or vessels, and the overall workflow involves repeated liquid transfers (by manual or robotic pipetting devices) between the different reaction vessels. In conventional workflows, each purification step typically involves removal of the nucleic acids from the previous reaction mixture by chemical extraction, precipitation, and/or adsorption to solid phases (such as microparticles or filters). Because of the inefficiencies in the multiple liquid transfer and purification steps, poor sample yield and loss of samples due to user error are major problems for complex molecular biology workflows (like those used in NGS).

SUMMARY

In some implementations, the current subject matter provides a system and method for microfluidic sample preparation. The preparation can be accomplished through the use of a single continuous flow technology, referred to as a "bump array", also referred to as determininstic lateral displacement ("DLD"), that can be used to manipulate and separate cells, organelles, microparticles, and high molecular weight ("HMW") deoxyribonucleic acid ("DNA") molecules that exhibit particle-like properties.

In some implementations, the current subject matter relates to a method for processing of a biological fluid. The method can include separating at least one first cell from the biological fluid, applying at least one first treatment to the at least one separated cell to produce a first treated solution, applying at least one second treatment to the first treated solution to produce a second treated solution, and processing at least one of the first treated solution and the second treated solution using a deterministic lateral displacement to generate an output solution.

In some implementations, the current subject matter can include one or more of the following optional features. The biological fluid can include at least one of the following: whole blood, urine, spinal fluid, saliva, buccal swabs, sputum, bronchial lavage, gastric lavage fluid, microbial culture media, feces, buffy coat, serum, plasma, platelet concentrate, water samples, and/or any other biological, chemical, and/or biochemical fluids and/or any combination thereof. The deterministic lateral displacement can use at least one bump array to process at least one of the first treated solution and the second treated solution. The deterministic lateral displacement can use a sequential arrangement of a plurality of bump arrays to process at least one of the first treated solution and the second treated solution.

In some implementations, the biological fluid can be whole blood. The applying of at least one first treatment can include lysing cells separated from the whole blood to generate a purified deoxyribonucleic acid ("DNA"). The applying of at least one second treatment can include combining the purified DNA with a transposase complex and at least one sequencing adaptor.

In some implementations, the method can further include fractionating the output solutions based on a size of at least one cell contained within the output solution.

In some implementations, the current subject matter can relate to a system for processing of a biological fluid. The system can include at least one input reservoir for receiving the biological fluid and separating at least one first cell from the biological fluid, at least one bump array mechanism coupled to the at least one input reservoir for applying at least one first treatment to the at least one separated cell to produce a first treated solution, applying at least one second treatment to the first treated solution to produce a second treated solution, and processing at least one of the first treated solution and the second treated solution using a deterministic lateral displacement to generate an output solution, and an output reservoir for receiving the output solution. In some implementations, the current subject matter can include various optional features discussed above and in the following text of the present disclosure.

In some implementations, the current subject matter relates to a method for processing a whole blood sample using a sequential and continuous arrangement of bump arrays integrated in a continuous flow operation. The method can include receiving the whole blood sample at a first bump array in the arrangement of bump arrays, purifying the whole blood sample to produce white blood cells, isolating nuclei from the white blood cells, isolating deoxyribonucleic acid ("DNA") from the nuclei, purifying DNA from the nuclei, and treating the purified DNA using at least one chemical and/or enzymatic DNA treatment.

In some implementations, the current subject matter relates to a method for processing of a fluid sample using at least one bump array. The method can include receiving the fluid sample at the at least one bump array, isolating, using the at least one bump array, at least one nucleic acid-containing cell and/or particle of interest from the fluid sample on the basis of a size of the cell and/or particle, contacting, using the at least one bump array, the isolated cell and/or particle with at least one reagent stream for releasing at least one nucleic acid from the cell and/or particles in substantially pure form, moving, using the at least one bump array, the at least one purified nucleic acids out of the reagent stream, and removing the at least one purified nucleic acid from the at least one bump array.

In some implementations, the current subject matter can include one or more of the following optional features. A plurality of bump arrays can process the nucleic acid, wherein individual bump arrays in the plurality of bump arrays can be connected in series, wherein an output of one bump array can be provided to an input of a subsequent individual bump array. Alternatively, a single bump array can be used for the receiving, the isolating, the contacting and the moving. The fluid sample can include at least one of the following: an avian whole blood and a mammalian whole blood and the nucleic acid-containing cells and/or particles can be white blood cells. The fluid sample can include at least one of the following: an avian whole blood and a mammalian whole blood, and the nucleic acid-containing cells and/or particles can be circulating tumor cells. The fluid sample can include at least one of the following: an avian whole blood and a mammalian whole blood, and the nucleic acid-containing cells and/or particles can include at least one of the following: white blood cells, bacteria, viruses, fungi, and parasitic protozoans.

The biological fluid can include at least one of the following: whole blood, urine, spinal fluid, saliva, buccal swabs, sputum, bronchial lavage, gastric lavage fluid, microbial culture media, feces, buffy coat, serum, plasma, platelet concentrate, water samples, and/or any other biological, chemical, and/or biochemical fluids and/or any combination thereof.

In some implementations, the current subject matter relates to a method for serially processing of a high molecular weight ("HMW") nucleic acid using at least one chemical and/or enzymatic reagent stream using at least one bump array, wherein HMW nucleic acid has an effective hydrodynamic radius that is greater than a critical size of the at least one bump array. The method can include receiving the HMW nucleic acid at the at least one bump array, and contacting the HMW nucleic acid with the at least one chemical and/or enzymatic reagent stream, wherein the at least one chemical and/or enzymatic reagent stream flows in the direction of bulk fluid flow through the bump array, whereas the HMW nucleic acid flows at an angle to the direction of bulk fluid flow. The HMW nucleic acid can react with the at least one chemical and/or enzymatic reagent stream.

In some implementations, the current subject matter relates to a method for serial processing of a nucleic acid using at least one chemical and/or enzymatic reagent stream using at least one bump array. The method can include receiving the nucleic acid, flowing the nucleic acid into the at least one bump array, contacting, using the at least one bump array, the nucleic acid with at least one chemical and/or enzymatic reagent stream, modifying, using at least one chemical and/or enzymatic reagent stream, the nucleic acid, and removing, using the at least one bump array, the purified nucleic acid from the at least one chemical and/or enzymatic reagent stream.

In some implementations, the current subject matter can include one or more of the following optional features. A plurality of bump arrays can serially process the nucleic acid, wherein individual bump arrays in the plurality of bump arrays can be connected in series, wherein an output of one bump array in the plurality of bump arrays can be input to the subsequent individual bump array in the plurality of bump arrays. Alternatively, a single bump array can perform the flowing, the contacting, the modifying, and the removing. The nucleic acid can be a high molecular weight ("HMW") nucleic acid. Alternatively, the nucleic acid can be a deoxyribonucleic acid ("DNA"), wherein the DNA can be bound to at least one microparticle for carrying the DNA through the bump array. The DNA can be bound using at least one of the following: covalent binding and non-covalent binding.

In some implementations, the current subject matter relates to a method for processing of a fluid sample using at least one bump array. The method can include receiving the fluid sample at the at least one bump array, isolating, using the at least one bump array, at least one nucleic acid-containing cell and/or particle of interest from the fluid sample on the basis of a size of the cell and/or particle, contacting, using the at least one bump array, the isolated cell and/or particle with at least one reagent stream for releasing at least one nucleic acid from the cell and/or particles in substantially pure form, modifying the nucleic acid, and moving, using the at least one bump array, the at least one purified nucleic acid out of the reagent stream, and removing the at least one purified nucleic acid from the at least one bump array.

In some implementations, the current subject matter can include one or more of the following optional features. The nucleic acid can be a high molecular weight ("HMW") nucleic acid. Alternatively, the nucleic acid can be a deoxyribonucleic acid ("DNA"), wherein the DNA can be bound to at least one microparticle for carrying the DNA through the bump array. The DNA can be bound using at least one of the following: covalent binding and non-covalent binding. The fluid sample can be serially processed using at least one chemical and/or enzymatic reagent stream using the at least one bump array. The nucleic acid can be modified using at least one chemical and/or enzymatic reagent stream. The modified nucleic acid can include at least one of the following: a deoxyribonucleic acid ("DNA") sequencing library and a recombinant DNA library.

In some implementations, the current subject matter relates to a reagent system for generating DNA sequencing libraries. The system can include a transposase reagent complexed with a linear DNA reagent, the DNA reagent having transposase recognition sequences and sequencing adapter sequences at each end of the DNA reagent, whereby on reaction with a DNA molecule targeted for sequencing, the transposase inserts the adapter-bearing linear DNA reagent into the sequencing target to form a cointegrate structure, wherein the sequencing target is cleaved at a single position, and the ends of the cleaved target are joined to the ends of the adapter-bearing linear DNA reagent.

In some implementations, the use of a singular separation technology that can accommodate multiple types of particles (e.g., cells, organelles, microparticles, and HMW DNA molecules) can provide for example, but not limited to, an ability to accomplish multiple sequential processing steps by a common process, in a single operation, and on a single consumable device. Further, in multi-step processes, integration of reaction and post-reaction cleanup steps can enable seamless, substantially zero-loss transfer of sample between processing steps. Sample purification can be accomplished on the basis of "particle" size alone. Thus, differential adsorption to a solid phase is not used and sample loss due to irreversible adsorption can be avoided. In some implementations, a portion of the initial sample that is retained in the system and either passed onto a further processing or collected at the end, can be purified after every step in each process by mechanisms, including, but not limited to, buffer exchange and removal of low molecular weight ("LMW") reagents. The current subject matter system can provide a hands-free means for a lengthy and complex sample preparation process that may be required for NGS. All of the processes can be performed by current subject matter systems and method substantially without user intervention, and, thus, user-mediated error and user-mediated variability can be substantially obviated. Bump array NGS processing can be used for routine, quality-control ("QC")-intensive applications like clinical trials and diagnostic testing.

In principle, input sample size can be scaled from 100's of microliters ("μl") of whole blood (e.g., 100 μl to 999 μl of whole blood) down to the single cell level, a feature that may accelerate sequencing applications in cancer research and diagnostics.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

The discussion in the present disclosure may refer to and/or use various terms in connection with describing various implementations of the current subject matter's systems and methods. The following definitions of such terms are provided for illustrative purposes only and are not intended to limit the scope of the current subject matter disclosed herein.

The term "sample" or "biological sample" can describe a plurality of particles that can be separated and processed by the bump array. Exemplary particles can include, but are not limited to, cells, nuclei, organelles, high molecular weight ribonucleic acid ("RNA") or deoxyribonucleic acid ("DNA") (RNA and DNA can be collectively referred herein as nucleic acid ("NA")), and microorganisms (e.g., bacterium and viruses) within a biological fluid or tissue. When particles are processed from intact tissue, such as a biopsy of a tumor or neoplasm, the cells are typically dissociated and resuspended in a fluid prior to introducing the particles into an array or system of some embodiments of the disclosure.

Figure 2:
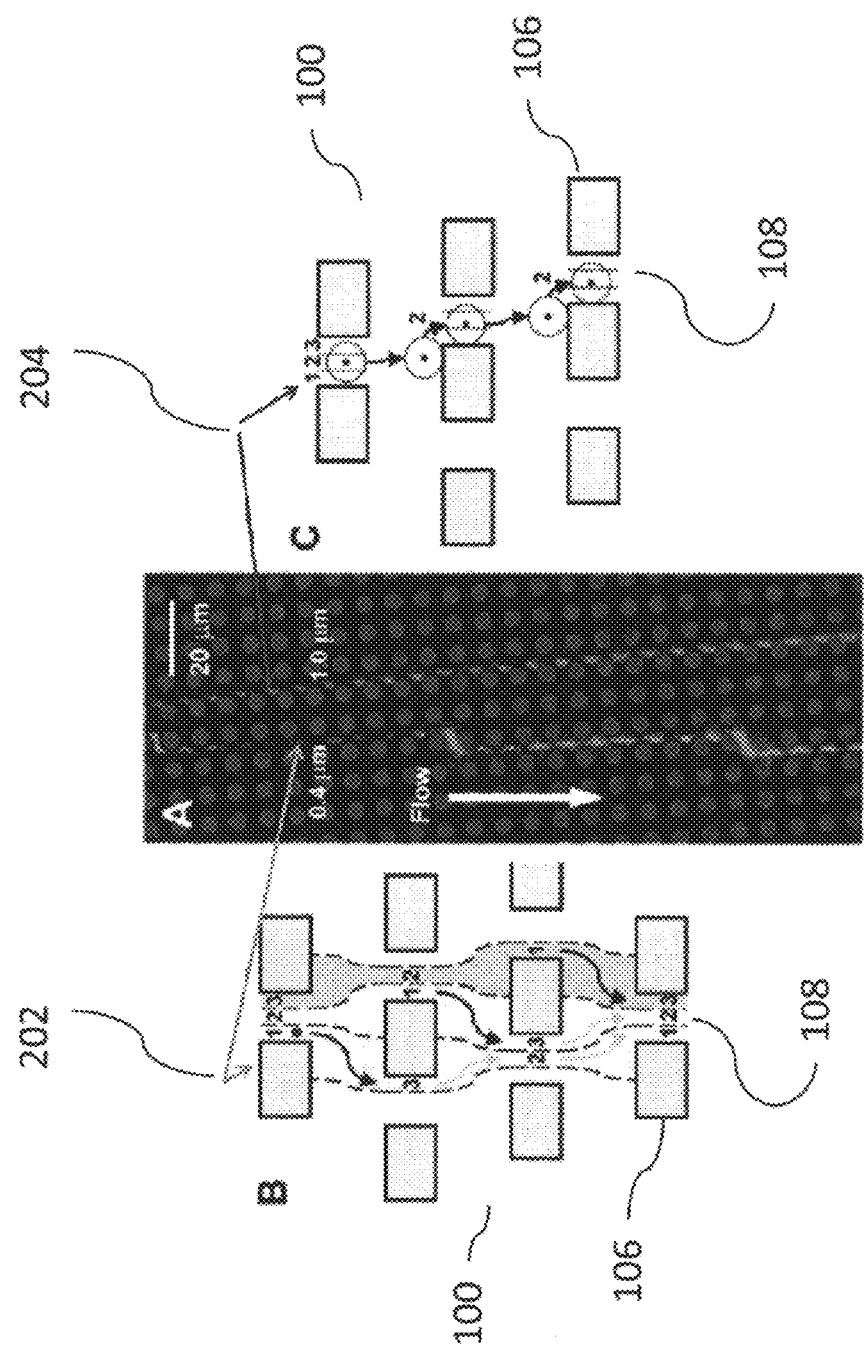
FIG. 2A is a photograph illustrating fluorescent microparticles 0.4 μm (green) and 1.0 μm (red) flowing through a bump array, $\lambda=8$ μm, $\lambda/d=10$.
FIG. 2B is a schematic diagram illustrating the trajectory of a particle having a smaller than the critical size for any given bump array.
FIG. 2C is a schematic diagram illustrating the trajectory of a particle having a greater than the critical size for any given bump array.
Figure 9:
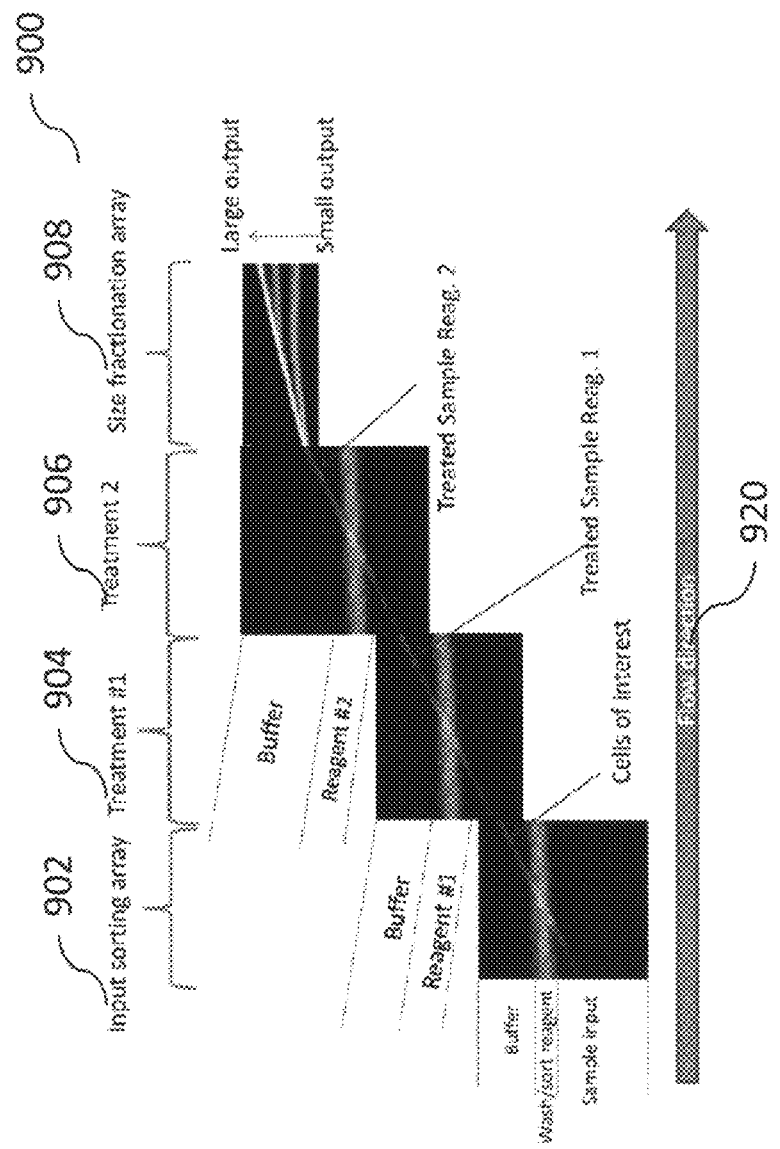
FIG. 9 illustrates in schematic form, an exemplary strategy for processing of a fluid sample, according to some implementations of the current subject matter.
Figure 10:
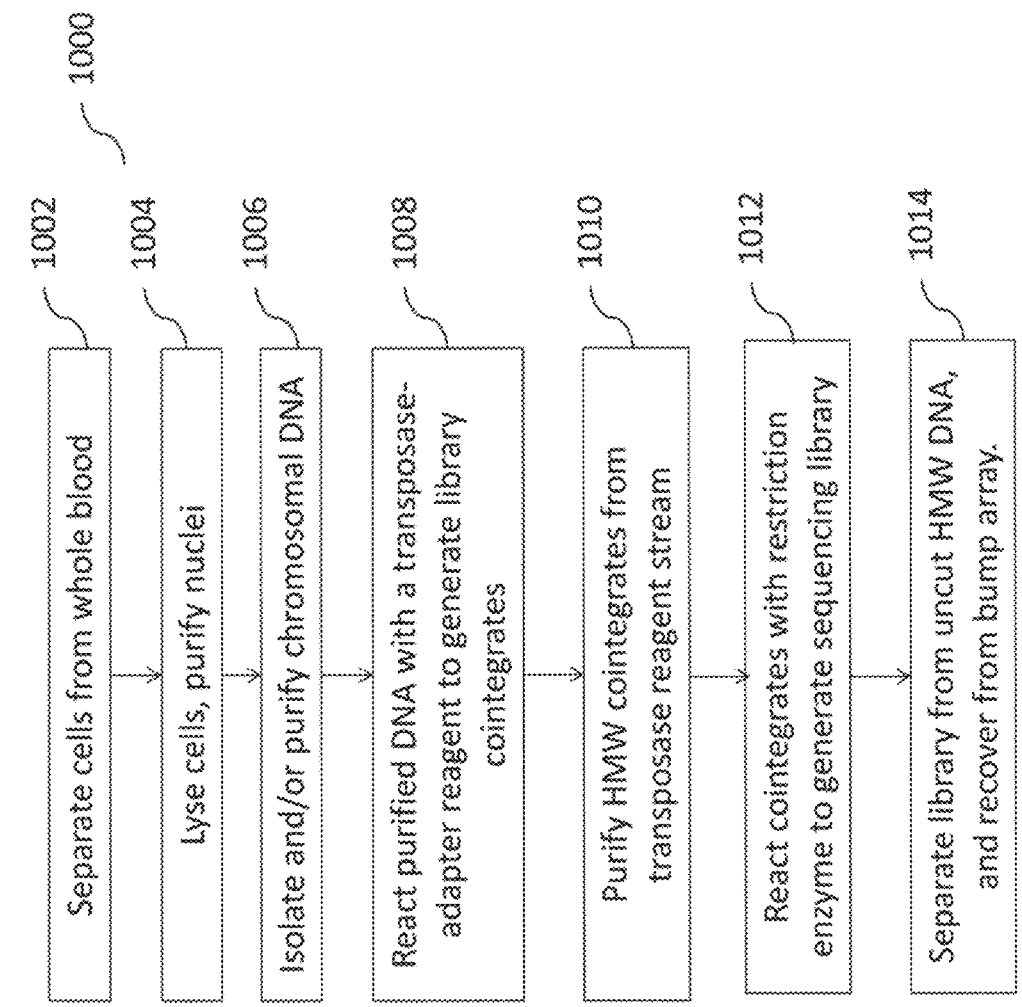
FIG. 10 is a method, according to some implementations of the current subject matter.

The term "fraction" can describe a subset of the particles within a sample. A fraction can be defined or determined by size. Alternatively, a fraction can be defined or determined by any physical property, such as size, that causes it to differentially traverse the field of posts in a bump array. For instance, fractions containing particles of smaller sizes can travel in pathways that more closely approximate the vector direction in which the primary fluid or stream flows across the array (for example, as shown in FIGS. 2B, 9 and 10). In contrast, fractions containing particles of larger sizes can travel in pathways that deviate further from the vector direction in which the primary fluid or stream flows across the array (i.e., they are diverted or bumped away from the main flow direction at a more severe angle) (for example, as shown in FIGS. 2C, 9 and 10).

An exemplary "sample" can include, but is not limited to, a cell, a nucleus, an organelle, a HMW RNA (intranuclear, intracellular, or extracellular), a HMW DNA (intranuclear, intracellular, or extracellular), a microorganism, a bacterium, a virus, or any combination thereof. "Biological fluids" can include, but are not limited to, aqueous humour and vitreous humour, bile, blood (whole blood, serum, plasma, cell-rich fractions), breast milk, cerebrospinal fluid ("CSF"), endolymph and perilymph, gastric juice, mucus (including phlegm), peritoneal fluid, pleural fluid, saliva, sebum (skin oil), semen, sweat, tears, vaginal secretion, vomit, and urine. "Biological tissues" can include, but are not limited to, those tissues derived from the endoderm, mesoderm, or ectoderm; those tissues that can be connective, muscle, nervous, or epithelial in nature; tissues that can include bone, cartilage, tendon, bone marrow, blood, vasculature (arteries and veins), smooth muscle, skeletal muscle, cardiac muscle (the heart), the central nervous system (brain, spinal cord, cranial nerves), peripheral nervous system (peripheral nerves), skin, respiratory tract, digestive tract, and reproductive tract.

Nucleic acids can be derived from genomic DNA, double-stranded DNA ("dsDNA"), single-stranded DNA ("ssDNA"), coding DNA ("cDNA"), messenger RNA ("mRNA"), short interfering RNA ("siRNA"), short-hairpin RNA ("shRNA"), microRNA ("miRNA"), single-stranded RNA, double-stranded RNA ("dsRNA"), a morpholino, RNA interference ("RNAi") molecule, mitochondrial nucleic acid, chloroplast nucleic acid, viral DNA, viral RNA, and other organelles with separate genetic material. Furthermore, samples can include nucleic acid analogs that can contain modified, synthetic, or non-naturally occurring nucleotides or structural elements or other alternative/modified nucleic acid chemistries known in the art. Additional examples of nucleic acid modifications can include the use of base analogs such as inosine, intercalators and minor groove binders. Other examples of nucleic acid analogs and alternative/modified nucleic acid chemistries can be used as well.

PNA oligomers can be included in exemplary samples or fractions of some embodiments of the disclosure. PNA oligomers can be analogs of DNA in which the phosphate backbone is replaced with a peptide-like backbone.

Polypeptides or proteins can be complex, three-dimensional structures containing one or more long, folded polypeptide chains. Polypeptide chains are composed of a plurality of small chemical units called amino acids. Naturally occurring amino acids can have an L-configuration. Synthetic peptides can be prepared employing conventional synthetic methods, using L-amino acids, D-amino acids or various combinations of L- and D-amino acids. The term "peptide" can describe a combination two or more amino acids. Naturally occurring amino acids have an L-configuration. Peptides having fewer than ten amino acids can be "oligopeptides," whereas peptides containing a greater number of amino acid units are "polypeptides." Any reference to a "polypeptide" also includes an oligopeptide. Further, any reference to a "peptide" can include polypeptides and oligopeptides. Each different arrangement of amino acids can form a different polypeptide chain.

The term "nucleic acid molecule" can describe the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. The term "nucleic acid molecule," and in particular DNA or RNA molecule, can refer only to the primary and secondary structure of the molecule, and does not limit it to any particular tertiary forms. Thus, this term can include double-stranded DNA found, in linear or circular DNA molecules (e.g., restriction fragments), plasmids, and chromosomes. A "recombinant DNA molecule" is a DNA molecule that has undergone a molecular biological manipulation.

Nucleic acids can be processed by chemical or enzymatic reactions within the bump array or system of some embodiments of the disclosure to impart fluorescent, magnetic, or radioactive properties to these molecules for the purpose of supporting sequence detection or analysis in subsequent analyses or for use in devices other than the bump arrays and systems described herein.

Regarding polypeptides, the term "native" can describe a non-denatured polypeptide. Polypeptides of according to some embodiments of the disclosure are native or denatured.

In some implementations, the current subject matter relates to systems and methods for processing biological fluids by using a "bump array" and/or multiple "bump arrays" and for creating next-generation sequencing libraries based on the processed biological fluids. In some implementations, the biological fluids can include, but are not limited to, whole blood, urine, spinal fluid, saliva, buccal swabs, sputum, bronchial lavage, gastric lavage fluid, microbial culture media, feces, buffy coat, serum, plasma, platelet concentrate, water samples, and/or any other biological, chemical, and/or biochemical fluids and/or any combination thereof. The bump array can be also referred to as a deterministic lateral displacement ("DLD") mechanism that can separate certain size molecules from a fluid.

In some implementations, the current subject matter can implement a series of bump arrays that can be integrated into one continuous flow operation, where one can use a crude biological sample as input and then process the sample by purifying the sample, isolating various components contained in the sample, such as, for example, molecules, cells, etc. from the sample, purifying isolated components and performing various treatments on the purified isolated components. For exemplary, illustrative and non-limiting purposes only, the following discussion will refer to whole blood as a biological sample being processed. However, it should be understood that the current subject matter is not limited to the use of whole blood and can include any of the above biological fluids as well as any others.

Assuming that the biological sample is whole blood, then the current subject matter's system can perform the following operations: purify white blood cells ("WBC") from the whole blood, isolate nuclei from the cells, isolate DNA from the nuclei, perform DNA purification from the nuclei, and perform various chemical and/or enzymatic DNA treatments on the purified DNA. In some implementations, any purified nucleic acids can be used for performance of various chemical and/or enzymatic DNA treatments on them. In some implementations, the current subject matter can allow a biological sample to be contacted with various reagents and removed from the reagent stream (as needed) using DLD. Further, in some implementations, the current subject matter can process smaller nucleic acids using bump array(s) by attaching the molecules to microparticles that are bumpable. In this way, the particles can be used to drag their DNA cargo through multiple reagent streams.

In some implementations, the current subject matter system can include at least one bump array device that can have one or more bump arrays. The bump array device can serially treat and purify nucleic acid fluid samples. Multiple cycles of treatment and purification can be carried out using a single flow device in a single continuous flow operation. The treatments can be chemical and/or enzymatic. The nucleic acids can be purified from cells and/or complex liquid biological sample, such as whole blood. The bump array device can also be used for performing various processing of the purified nucleic acids. Non-limiting examples of such processing can include at least one of the following: phosphorylation, dephosphorylation, restriction digestion, ligation, denaturation, hybridization, processing by polymerases, fluorescent or radioactive labeling, chemical modification of DNA bases or backbone groups, enzymatic or chemical excision of modified bases, staining of nucleic acids with chromophores or fluorophores, etc. and/or others and/or any combination thereof. The nucleic acids can be particle bound nucleic acids, where nucleic acids can be attached to microparticles. This can allow for processing of small nucleic acids. The particles can render the attached nucleic acids bumpable in arrays with easily manufactured array dimensions.

In some implementations, the current subject matter can provide a system and a method for processing of fluids. The processing can include purification of fluids which can be accomplished by flowing a complex fluid sample into a bump array, using a bump array to isolate nucleic acid-containing cells or particles of interest on the basis of particle size, using a bump array to contact isolated particles with one or one reagent streams that can release nucleic acid from the particles in substantially pure form, and using a bump array to move purified nucleic acids out of the reagent stream. Once the purified nucleic acids are moved out of the reagent stream, the purified nucleic acids can be substantially free from other cellular and sample components and can be substantially free from reagent stream components of the bump array.

In some implementations, the individual bump arrays can be connected in series so that the product output of one bump array can be connected to the sample input of the subsequent individual bump arrays. In some implementations, the same bump array can be used for all steps. Furthermore, cell fractionation and reagent treatments can be accomplished in physically distinct regions of a single bump array. In some implementations, the input sample can be avian or mammalian whole blood and the nucleic-acid-containing particles can be white blood cells. In some implementations, the input sample can be avian or mammalian whole blood and the nucleic-acid-containing particles can be circulating tumor cells. In some implementations, the input sample can be avian or mammalian whole blood and the nucleic-acid-containing particles can be white blood cells, bacteria, viruses, fungi, parasitic protozoans and/or any others and/or any combination thereof.

In some implementations, the current subject matter can provide a serial processing of high molecular weight nucleic acids by chemical and enzymatic means on bump arrays. The HMW nucleic acid can have an effective hydrodynamic diameter that can be greater than the critical diameter of the bump array and the HMW nucleic acid can be contacted with at least a first reagent stream, where the first reagent stream can flow in the direction of bulk fluid flow and where the HMW nucleic acid is bumped through the first reagent stream and can react with the first reagents.

In some implementations, the current subject matter can provide a serial processing of HMW nucleic acids by one or more chemical or enzymatic means that can be accomplished by flowing a sample of HMW nucleic acids into a bump array, using a bump array to contact HMW nucleic acids with at least one reagent streams that can modify the nucleic acids (e.g., chemically, enzymatically, etc.), and, optionally, using a bump array to remove purified nucleic acids from the reagent stream.

In some implementations, the bump arrays can be individual bump arrays connected in series so that the product output of one bump array can be connected to the sample input of the subsequent individual bump arrays. The bump arrays can be the same bump arrays (and the cell fractionation and reagent treatments can be accomplished in physically distinct regions of one continuous bump array). Further, assuming that the DNA sample can be bound (covalently or noncovalently) to microparticles, the microparticles can be bumpable and can therefore act as carriers to take the DNA through the modification reactions.

In some implementations, the current subject matter can provide for processing of whole blood to produce a pure nucleic acid, which can be used to produce a modified pure nucleic acid. The modified pure nucleic acid can be a DNA sequencing library and/or a recombinant DNA library.

In some implementations, the current subject matter can provide a system that can accept a whole blood sample as input and produce a genomic DNA library suitable for next-generation sequencing ("NGS"). Library construction can take place in a single automated process without any user intervention. The system can lower the cost and labor of NGS sequencing and accelerate movement of NGS technology into diagnostic settings. The system can be scalable to accommodate samples containing very few cells (e.g., a single cell level), which can be important in treatment of cancer and/or other important medical problems.

In some implementations, the system can include a microfluidic, continuous-flow design. Liquid samples containing particles (e.g., cells, nuclei, and large macromolecules such as randomly-coiled HMW DNA) can be pumped through flow cells that can be populated by a regular array of micron-sized posts. The spacing and alignment of the posts can be arranged so that particles above a certain critical size can be "bumped" by the posts into a flow path that runs diagonally across the direction of bulk liquid flow. In contrast, sample components smaller than the critical size can travel straight along with the bulk flow. Using this mechanism, larger sample components can be separated and purified from smaller components laterally across the chip.

Samples can flow through these bump arrays under conditions of laminar flow (Reynolds number, $R_e$, <<1), so that discrete reagent streams can be introduced into arrays without significant lateral mixing. Large particles can be bumped diagonally into, and out of, such reagent streams to perform chemical or enzymatic reactions on the particles. The current subject matter system can use this principle to purify leukocyte nuclei, purify DNA, and enzymatically modify DNA for generation of NGS libraries.

Although the following steps are illustrated using a blood sample, this process can be performed on any biological fluid and/or any tissue sample from which the corresponding cells have been dissociated from one another and re-suspended in a fluid (as illustrated in Table 1 below). The isolation of foreign cells from a host can also be performed. For example, the raw material can be whole blood and/or a cell solution derived from whole tissue, but the intermediate fraction of interest can be a virus, a prokaryotic cell that is not native to the host (such as a bacterium), a parasite, a fungus, a pathogenic microbe, and/or any other fraction, component, fluid, etc., and/or any combination thereof.

TABLE 1

Raw Materials, intermediates, and processed output (also preferred embodiments) of bump array.

| Raw Input (biological fluid or Cell solution derived from tissue) | Intermediate(s) | Processed Output | Preferred Processed Output |
| --- | --- | --- | --- |
| Whole Blood | White Blood Cell(s) (WBC(s)) | Isolated and/or purified total DNA | NGS Library |
| Whole Blood | Cell-free fraction | Isolated and/or purified cell-free DNA | NGS Library |
| Tumor Biopsy | Isolated and/or purified tumor cell(s) | Isolated and/or purified total DNA from a single tumor cell | NGS Library for a single cell |
| Buccal Swab/spit | | Isolated and/or purified total DNA | NGS Library |
| High Molecular Weight (HMW) DNA | Fragmented DNA | Size-fractionated DNA | NGS Library, Recombinant Library |
| Bacterial/eukaryotic cultured cells | | Isolated and/or purified total DNA | NGS Library, Recombinant Library |

TABLE 1-continued

Raw Materials, intermediates, and processed output (also preferred embodiments) of bump array.

| Raw Input (biological fluid or Cell solution derived from tissue) | Intermediate(s) | Processed Output | Preferred Processed Output |
|---|---|---|---|
| Infected blood | Microbial cells | HMW microbial DNA | NGS Library |
| Liquid Microbial Culture | Microbial cells | HMW microbial DNA | NGS Library |
| Urine | Microbial cells | HMW microbial DNA | NGS Library |
| Spinal Fluid | Microbial cells | HMW microbial DNA | NGS Library |

Figure 1:
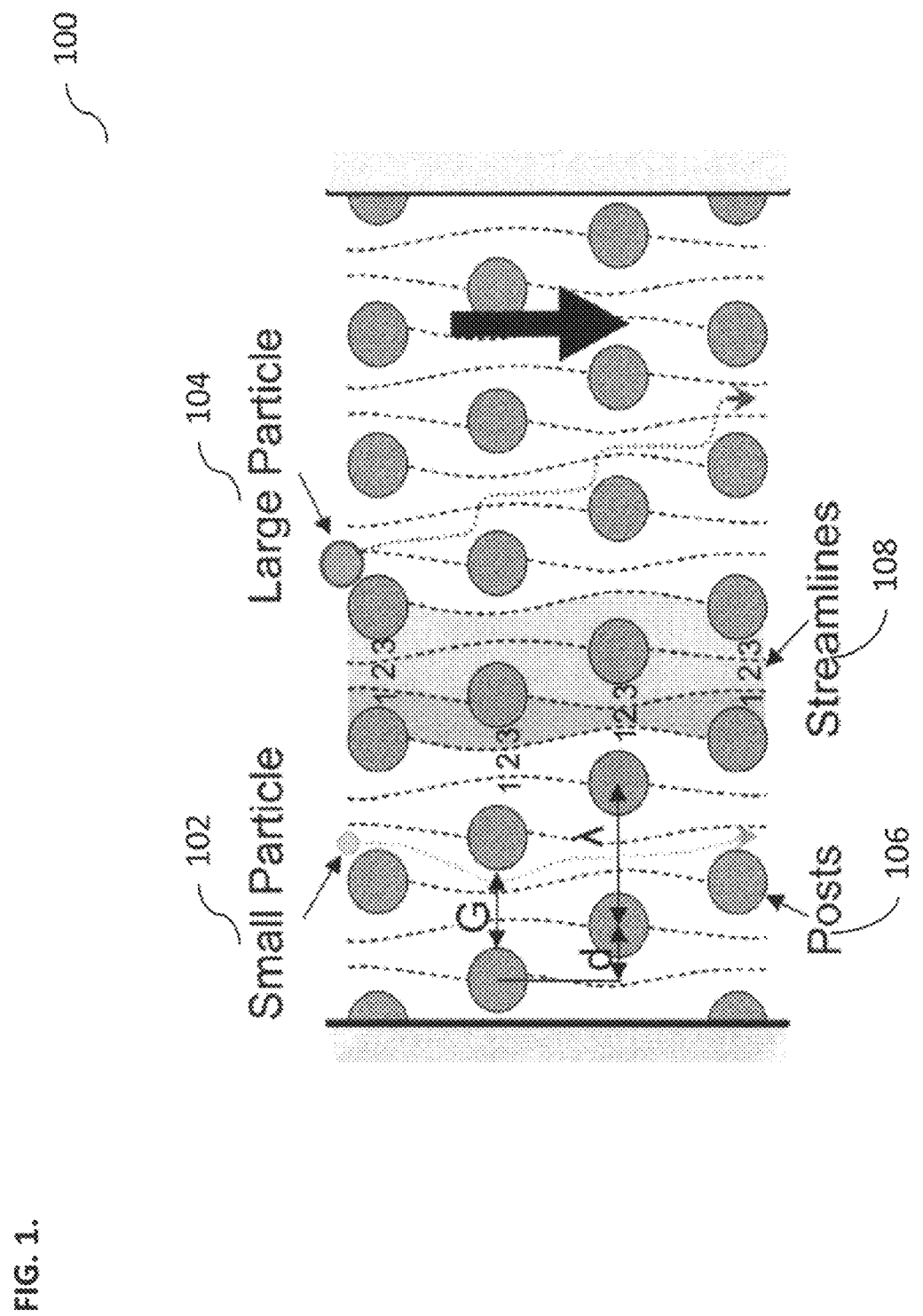
FIG. 1 is a schematic diagram illustrating an exemplary bump array.

FIG. 1 is a schematic diagram illustrating an exemplary bump array 100 (an exemplary bump array is illustrated in Davis J A, Inglis D W, Morton K J, Lawrence D A, Huang L R, Chou S Y, Sturm J C, Austin R H. "Deterministic hydrodynamics: taking blood apart." Proc Natl Acad Sci USA. vol. 103, 14779-84. 2006, which is incorporated herein by reference in its entirety). The bump array 100 can include a plurality of posts 106 and a plurality of streamlines 108, where the posts can be disposed in the streamlines 108 in a predetermined fashion, in a random fashion, and/or in any other desired way. The posts 106 can be disposed a predetermined distance G from one another, thereby creating a gap allow molecules, particles, etc. 102, 104 to move between the posts in the streamlines 108. The posts 106 can be disposed in accordance with a predetermined horizontal spacing $\lambda$ and can have a predetermined row offset d, as shown in FIG. 1. In some implementations of bump array applications, the parameters G, $\lambda$, and/or d can be particularly selected for the specific dimensions of the particles being separated by the bump array 100. Such exemplary design considerations are discussed by Inglis et al. (Inglis D W, Davis J A, Austin R H, Sturm J C. "Critical particle size for fractionation by deterministic lateral displacement." Lab Chip. vol. 6, 655-8. 2006, incorporated herein by reference in its entirety). As shown in FIG. 1, various size particles (e.g., small particles 102 and large particles 104) can move through the bump array 100 in a predetermined fashion (as shown by the arrows).

Liquid sample with particles flows vertically through regular post array (shown by the arrow in FIG. 1), with horizontal post spacing of $\lambda$, and row offset, d, will generate $\lambda/d$ liquid streamlines in each gap. Particles 104 with radius greater than the width of the first streamline are bumped diagonally (passing from streamline 1 to 2) at every gap. Small particles 102 with a radius smaller than the width of streamline, stay in the same streamline and pass vertically down the array with no lateral displacement.

FIG. 2A is illustrating fluorescent microparticles 202 having a diameter of 0.4 µm (green) and microparticles 204 having a diameter of 1.0 µm (red) flowing through a bump array, $\lambda$=8 µm, $\lambda/d$=10. The green particles 202 are smaller than the critical dimension for bumping and travel straight down along the lines of bulk liquid flow. The particles 202 can follow a zigzag streamline 108 path between the posts 106 with no lateral displacement, as shown in FIG. 2B. The trajectory of the particle 202 having a smaller diameter than the critical size for the bump array 100. While the path of the particle 202 follows a zigzag pattern around the posts 106, its flow continues in same direction as the general flow of the fluid sample being processed in the bump array 100. The red particles 204 can be larger than the critical dimension and can be bumped along a diagonal streamline 108 path across the array 100, as shown in FIG. 2C. The trajectory of the particle 204 can follow an angled trajectory with respect to the general flow of the fluid sample through the bump array 100, because the particles 204 can be bumped diagonally away from the posts 106. In some implementations, the bump array 100 can be used for cell sorting, size selection of large DNA (>20 kb), and microparticle size selection.

Figure 3:
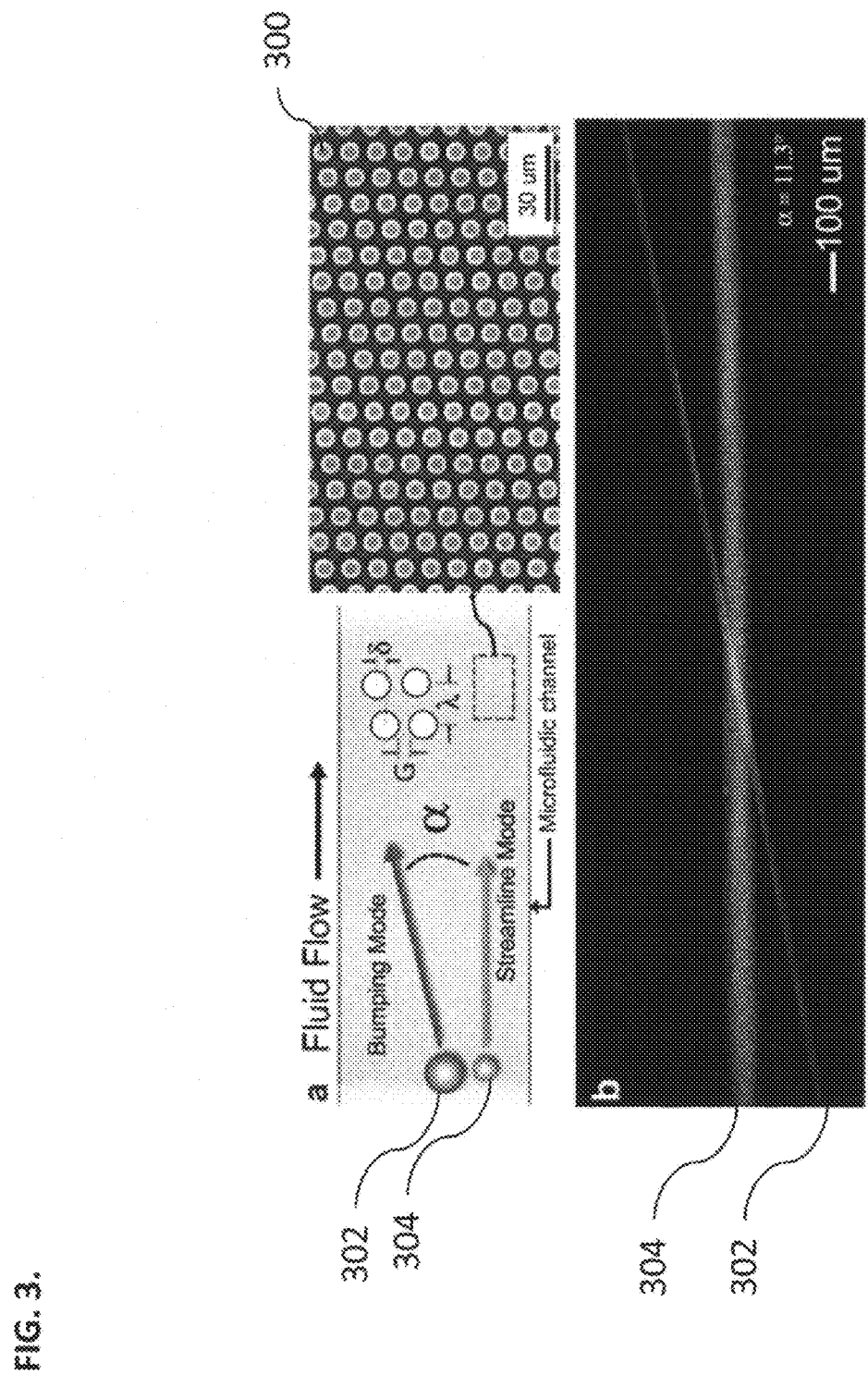
FIG. 3A is a schematic diagram illustrating an exemplary bump array for moving particles in and out of reagent streams, including a blow up of the texture of the obstacles on the chip.
FIG. 3B is a photograph of the exemplary bump array shown in FIG. 3A.
Figure 4:
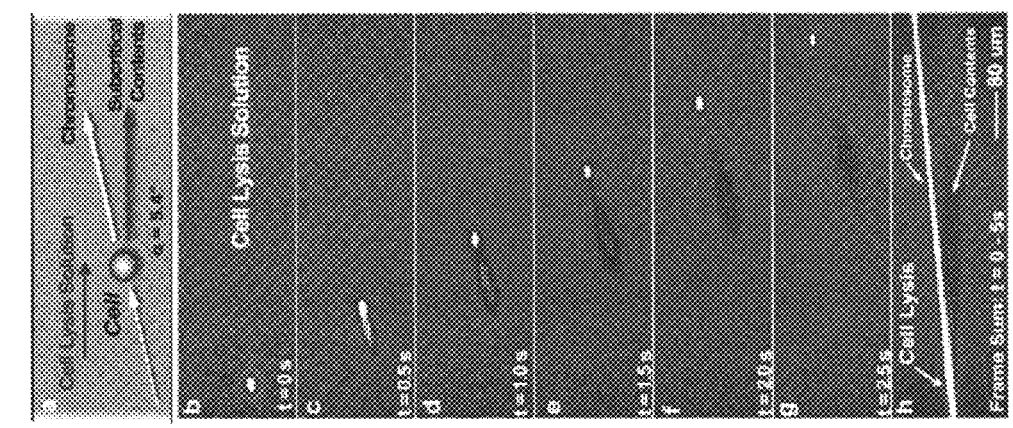
FIG. 4A-H is a series of photographs illustrating the lysis of an *E. coli* cell in a bump array.

FIG. 3A is a schematic diagram illustrating a bump array 300 for moving particles in and out of reagent streams (shown on the left of FIG. 3A), including a blow up of the texture of the obstacles on the chip (shown on the right of FIG. 3A). FIG. 3B illustrates the bump array 300 shown in FIG. 3A. 3 µm fluorescent beads 302 enter array at lower left and are bumped through a simulated reagent stream marked with non-bumpable 0.5 µm beads 304.

FIG. 4A-H is a series of photographs depicting the lysis of an E. coli cell in a bump array. Spheroplasted cell expressing fluorescent protein ("GFP") was stained with fluorescent DNA dye and bumped into SDS lysis stream located in top half of flow cell. Comet tail is released GFP. Nucleoid remains compacted and continues to bump diagonally. GFP is below critical size, and travels with flow.

Figure 5:
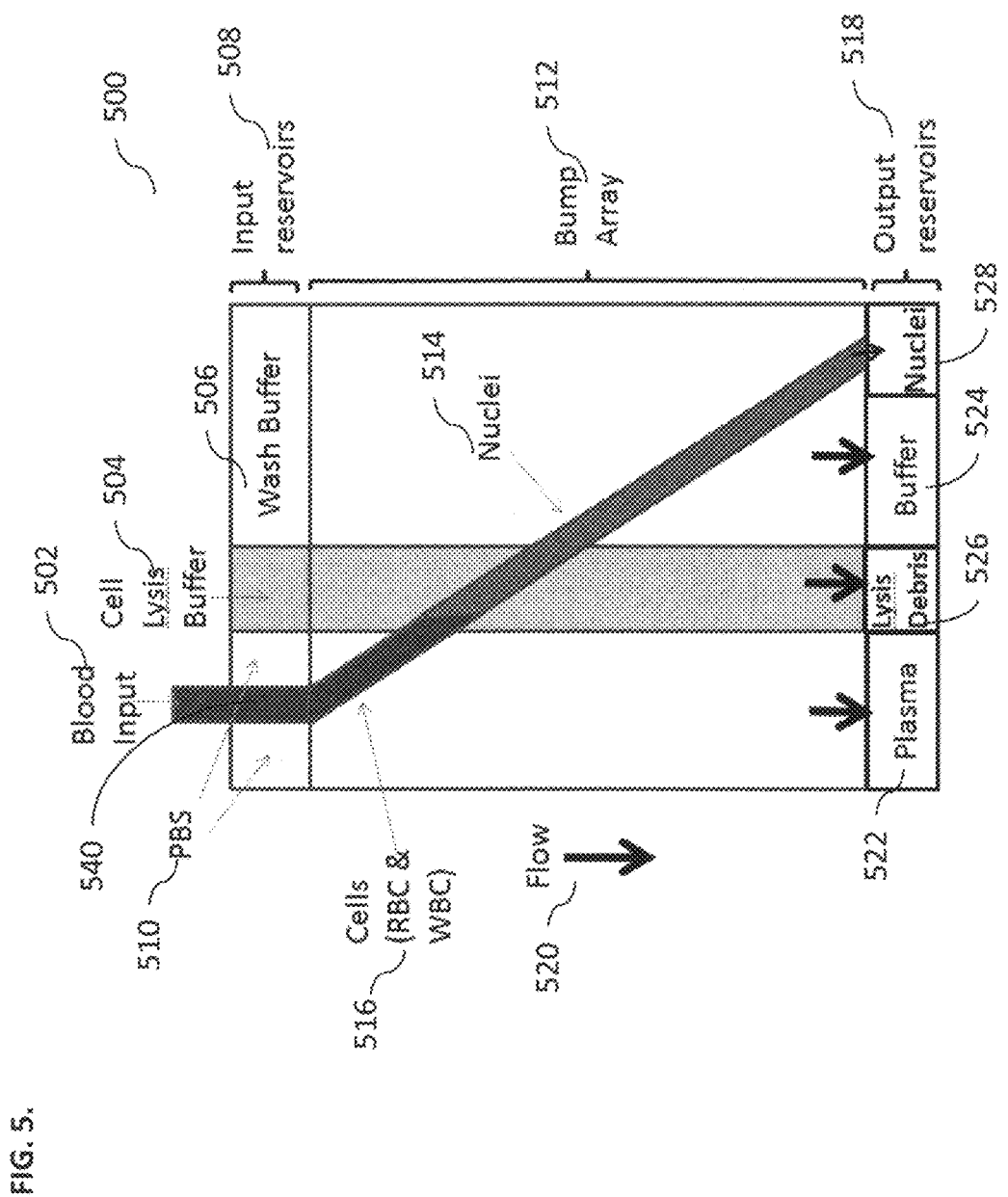
FIG. 5 illustrates an exemplary system for processing of a fluid sample, according to some implementations of the current subject matter.

FIG. 5 illustrates an exemplary system 500 for processing of a fluid sample, according to some implementations of the current subject matter. The system 500 can process a blood sample 502 as input. The system 500 can include at least one input reservoir 508, a bump array 512, and at least one output reservoir 518. The components of system 500 can be implemented in a single housing, separate housings that can be connected to one another, and/or in any other fashion. The bump arrays 512 can be a bump array shown in FIG. 1 and/or a plurality of bump arrays shown in FIG. 1 that can be sequentially coupled and/or connected to one another for the purposes of processing blood sample 502. The fluid sample can flow in a direction 520 from the input reservoirs 508 to output reservoirs 518, as shown in FIG. 5. The input reservoirs 508 can include reservoirs of phosphate buffered saline ("PBS") 510, on either side of the blood input port, a cell lysis buffer 504, and a wash buffer 506. The blood sample enters at the separate input port (or inlet) 540 and is treated to generate cells 516 (e.g., RBC, WBC, etc.) that enter the bump array 512 for processing. In some implementations, the bump array can include a particular and separate input port 540 that is designed to receive the blood sample 502. As such, the input port 540 (and other input ports shown and discussed in connection with FIGS. 6 and 7 below) can serve as a discrete input port that is physically separate from the other input reservoirs 504 and 506. The blood sample input port 502 can be always physically distinct and discrete from the surrounding buffer input ports so that the sample path is well defined and, further, so that the desired product can come out in a relatively well defined position at the bottom output region. In some implementations, the output reservoirs can be not so well-defined as the input reservoirs, except for a physically discrete output reservoir that receives the desired output (as there is a desire to keep it from mixing with other waste streams). The cells are further lysed using the cell lysis buffer 504 to generate nuclei 514 that are further processed in the bump array 512. While the blood sample is being processed, the cells 516, the nuclei 514, and the remainder of the blood sample are being processed in the bump array 512. The remainder of the blood sample gets deposited as plasma 522 in the output reservoir. The remainder of the lysing process in the cell lysis buffer 504 can be deposited in the lysis debris output reservoir 526. The nuclei 514 are deposited in the nuclei output reservoir 528 and the remainder of the wash buffer solution can be deposited in the buffer output reservoir 524. System 500 can be used to perform processing operations 1002 and 1004 shown and discussed below in connection with FIG. 10 and can be designed to purify cells (e.g., leukocytes) from biological fluids, such as blood, and nuclei from lysed cells.

Figure 6:
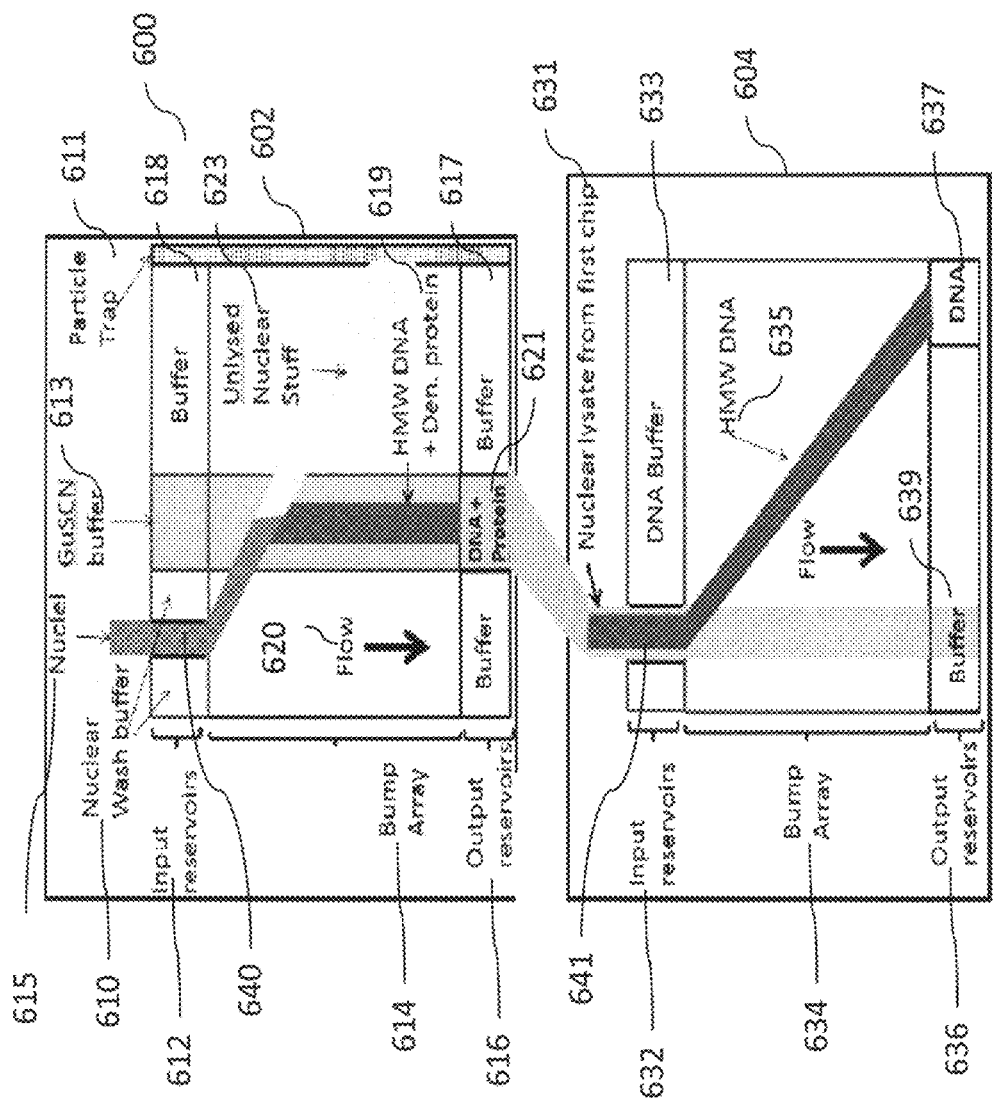
FIG. 6 illustrates another exemplary system for processing of a fluid sample, according to some implementations of the current subject matter.

FIG. 6 illustrates another exemplary system 600 for processing a fluid sample, according to some implementations of the current subject matter. The system 600 can include two separate components or "chips" 602 and 604 that can process fluid samples. The chip 602 can have a relatively large critical size for bumping that can be appropriate for the nuclei sample input. The system 600 can be used to purify high molecular weight ("HMW") DNA from isolated cell nuclei. The chip 602 can include input reservoirs 612, a bump array 614, and output reservoirs 616. The chip 602 can include a particle trap 611. The chip 602 can include a separate input port (or inlet) 640 for receiving the nuclei. The chip 604 can include input reservoirs 632, a bump array 634, and output reservoirs 636. The chip 604 can include a separate input port (or inlet) 641 for receiving the materials that have been processed by the chip 602, i.e., DNA+protein 621. The bump arrays 614 and 634 can be similar to the bump array shown in FIG. 1. The general direction of the fluid flow through the chips 602, 604 is indicated by an arrow 620.

The chip 602 can include a nuclear wash buffer 610, a guanidine isothiocyanate (GuSCN) buffer 613, and a buffer 618 (which can be similar to a wash buffer 506 shown in FIG. 5). The nuclei 615 enter the separate input port 640 and are then processed through the GuSCN buffer 613 in the bump array 614. The GuSCN can dissociate the nuclei and remove all nuclear proteins 619 from the DNA. The DNA and proteins have a smaller effective diameter than the critical size for bump array 602, and they flow out of the array with the GuSCN lysis reagent stream at outlet reservoir 621, as any unlysed nuclear material 623 is directed to the particle trap 611. HMW DNA and protein 619 flow into DNA+protein output reservoir 621, which is then routed for further processing to the sample input reservoir channel of chip 604.

The HMW DNA and protein 619 can be received as nuclear lysate from the chip 602 in the input reservoirs 632 (and, in particular, the input reservoir 641). Similar to FIG. 5, the input reservoirs 640 and 641 in the chips 602 and chip 604, are specifically designated to prevent mixing with any other materials present. The bump array of 604 can have a smaller critical size appropriate for bumping HMW DNA in the lysed sample. The DNA can be bumped rightward into DNA buffer (typically about 10-50 mM Tris-HCl, pH 7.5-8.0, and about 1-5 mM EDTA) away from the GuSCN and denatured nuclear proteins which flow with the bulk fluid path (down). The DNA 635 can exit the bump array at output reservoir 637 of the chip 604's output reservoirs 636. The remainder of the waste lysis stream and wash buffer can be deposited in the buffer output reservoir 639. The system 600 can be used to perform operation 1006 shown and discussed below in connection with FIG. 10.

Figure 7:
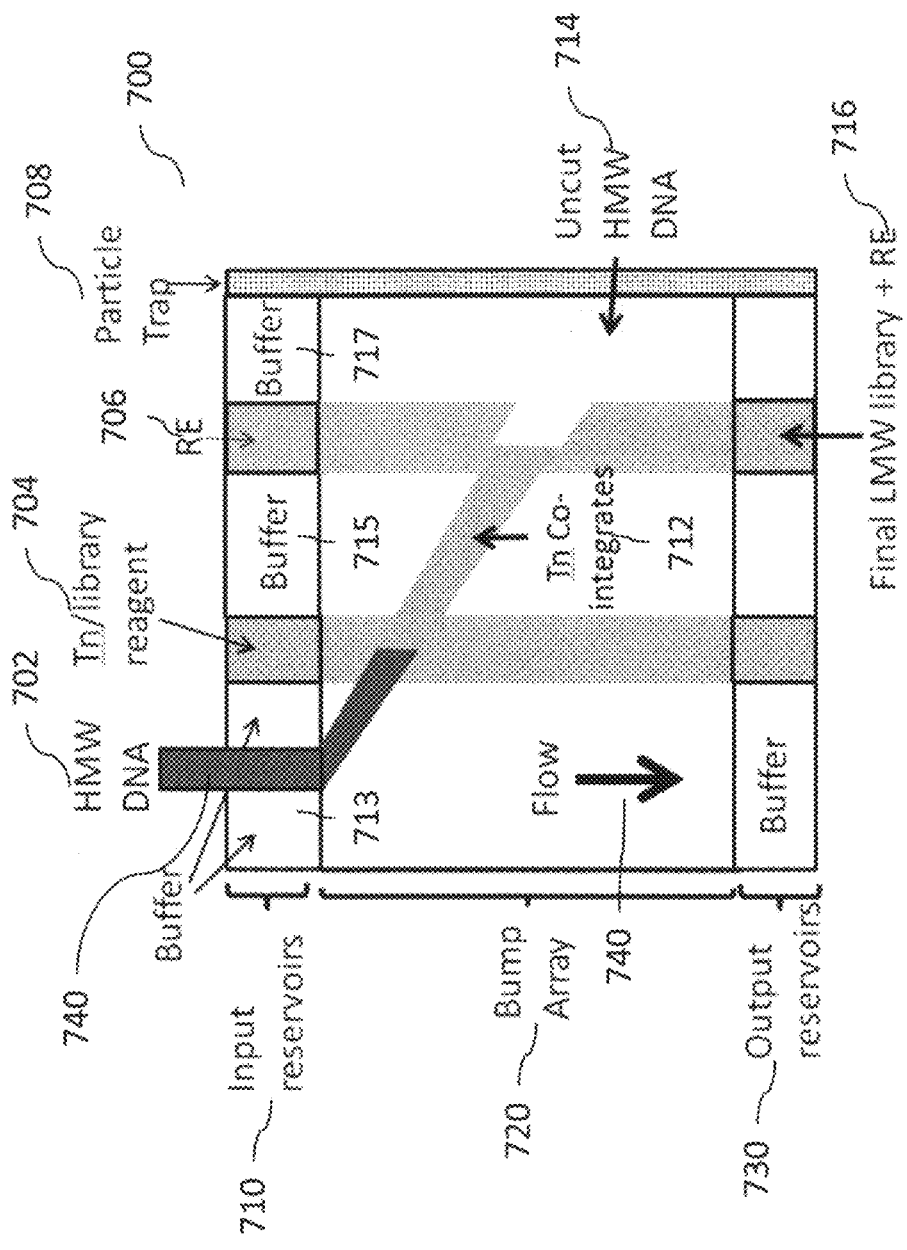
FIG. 7 illustrates another exemplary system for processing of a fluid sample, according to some implementations of the current subject matter.

FIG. 7 illustrates another exemplary system 700 for processing of a fluid sample, according to some implementations of the current subject matter. The system 700 can include input reservoirs 710, a separate input port (or inlet) 740 for receiving HMW DNA sample, a bump array 720, and output reservoirs 730. Each input reservoir 710 can be discrete to prevent dilution and/or mixing of components. The general direction of the fluid sample flow in the system 700 is indicated by the arrow 740. The input to the system 700 can be HMW DNA 702, which can be received in the separate input port 740 and is bumped through buffer entering the array immediately to the right of the input port. The HMW DNA 702 can then enter transposase reagent stream 704 where the HMW DNA can be modified with sequencing library adapters as shown in FIG. 8. As shown in FIG. 8, reaction with the transposon reagent of the current subject matter, produces HMW co-integrates that are still bumpable. The co-integrates 712 are bumped into a wash buffer region fed by reservoir 715, in order to remove free adapter substrates and transposase from the DNA. Then, the treated material can be further bumped into a restriction enzyme reagent stream 706 to which cleaves the adapters at engineered positions (see FIG. 8B) to liberate the final sequencing library. The final library is low in molecular weight and therefore no longer bumpable. As a result, the final library 716 can exit the bump array in the restriction enzyme reagent stream 716. Treatment with reagent 706 can result in the final low molecular weight library and reagent 716 deposited in an output port (or outlet) that can be specifically designated to receive the final LMW library+reagent and to prevent mixing of the final LMW library+reagent with any other output compounds of this process. HMW DNA that is not processed by the transposase/restriction enzyme streams remains HMW and can pass into the particle trap 714 at the far right side of the array. System 700 can be used to perform operation 1008, 1010, 1012, 1014 shown and discussed in connection with FIG. 10.

Figure 8A:
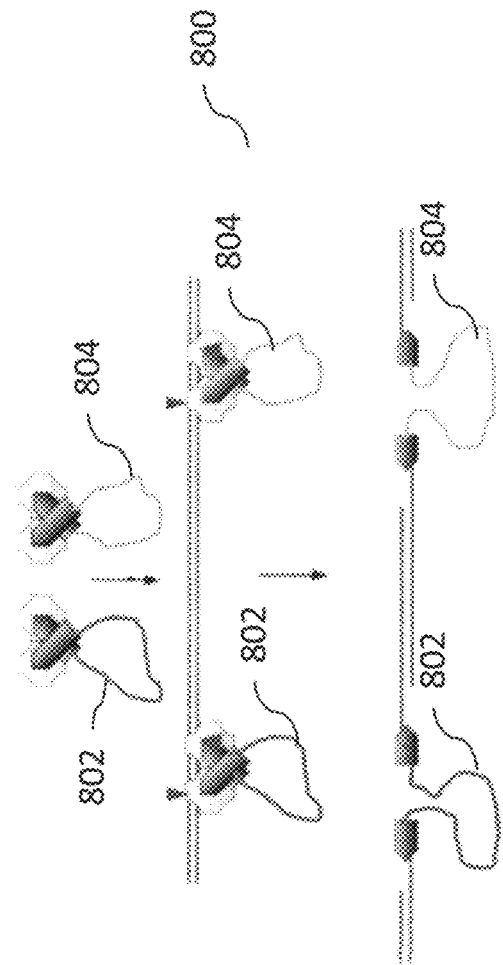
FIG. 8A is a schematic diagram illustrating a transposition-mediated library generation system optimized for use in automated bump array instrument.
Figure 8B:
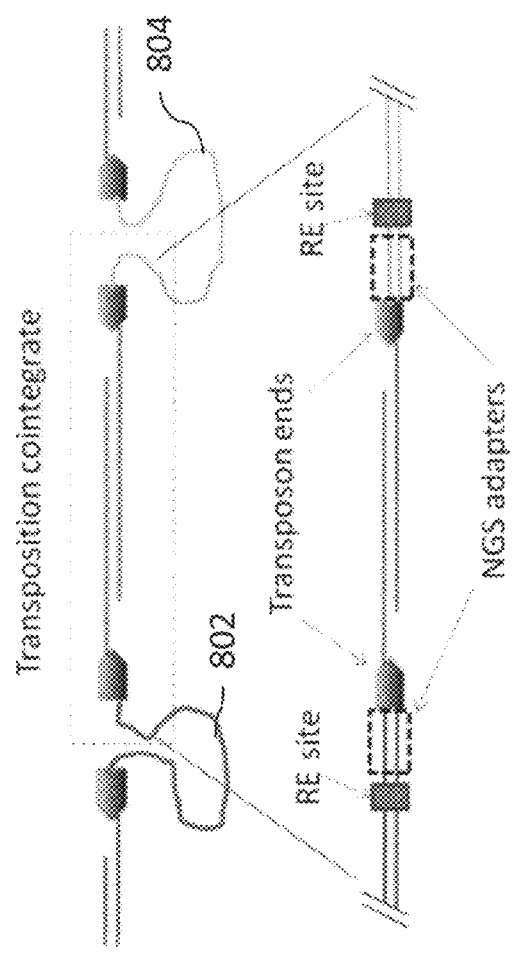
FIG. 8B is a schematic diagram illustrating a structure of transposition cointegrates.

FIG. 8A is a schematic diagram illustrating a transposition-mediated library generation system 800 that can be optimized for use in automated bump array instrument. Transposase enzymes can be loaded with linear recombinant transposon substrates. Lines 802 and 804 represent dsDNA substrates. Transposition reactions can insert the linear transposon substrates into the HMW DNA targets. The co-integrate product DNA can remain high in molecular weight after transposition, and therefore it can be bumped away from the transposon reagent stream after reaction. FIG. 8B is a schematic diagram depicting the structure of transposition cointegrates. NGS adapter sequences can be located adjacent to the transposon ends and allow sequencing into the insert from either end. The final library can be cleaved out of the HMW co-integrate by cleavage at engineered restriction enzyme sites that release the adapter-terminated sequencing library from the rest of the co-integrate (final cleavage not shown).

Although production of NGS libraries can be one of the exemplary embodiments of the current subject matter, there can be many other applications of the system. FIG. 9 illustrates this point schematically, shown an exemplary system 900 that can utilize multiple bump array step in serial fashion for performing multiple sequentially ordered processing steps on a fluid sample, according to some implementations of the current subject matter. The system 900 can have components that can be similar to the components in any of the systems shown and described in connection with FIGS. 1-7 above. The system 900 can include an input sorting array 902, a first treatment mechanism 904, a second treatment mechanism 906, and a size fractionation array 908. The fluid sample that enters the system 900 can flow in a general direction 920. The sample input that enters the input sorting array 902 can be washed and/or sorted using at least one reagent, where various "cells of interest" can be produced. Other components can be deposited in a buffer. The cells of interest can be treated using the first treatment mechanism 904, which can include a first reagent and an appropriate buffer. Treatment by the first treatment mechanism 904 can result in a first treated sample-reagent combination. The first treated sample-reagent combination is then processed by the second treatment mechanism 906, which can include a second reagent and an appropriate buffer. Treatment by the second treatment mechanism 906 can result in a second treatment sample-reagent combination that is passed on to a size fractionation array 908, which can sort the combination from small to large particles accordingly.

The system can retain flexibility regarding how these processes can be combined. Each of the five processes can be carried out in single-function flow chips that can be chained together serially. In this configuration, the product of each chip can be fed into the input port of the subsequent chip. Alternatively, multiple steps can be carried out on the same chip by using multiple reagent streams separated laterally across the chip, and changing the array dimensions laterally across the chip to match the size of the intermediates that need to be bumped at each stage.

FIG. 10 illustrates a method 1000 for sequentially processing blood samples using bump arrays, according to some implementations of the current subject matter. At 1002, cells can be separated from a biological fluid, such as whole blood. A few microliters ("µl") of whole blood can be obtained. Blood cells can be separated from plasma. Cells can be washed with a buffer stream as they are separated from the plasma. At 1004, cells can be lysed. Washed cells can be lysed by bumping them through a reagent stream containing non-ionic detergent. After removing the lysis reagent, intact leukocyte nuclei can be bumped diagonally through a wash buffer stream. Cytoplasmic contents are too small to bump and can be carried out of the array in the detergent lysis stream. At 1006, chromosomal DNA can be isolated and/or purified. Washed leukocyte nuclei can be bumped through a nuclear lysis reagent stream to remove all lipid and nuclear proteins from the HMW chromosomal DNA. The array dimensions can be chosen so that HMW DNA, in its double-stranded random-coil configuration, can be bumped diagonally out of the lysis reagent stream. All nuclear lipids, RNA, and proteins may be too small to bump, and can be carried out of the array in the lysis stream. At 1008, purified DNA can be reacted with a transposase-adapted reagent to generate library cointegrates. Purified HMW DNA can be bumped through a reagent stream containing a transposase complex that can be preloaded with sequencing-adapter-modified transposon ends. The current subject matter can provide a transposase complex in which the transposon-adapted ends of the trans-posasome can be on the same linear piece of DNA. As a result, in this system, a reaction of the transposasome with the HMW DNA can generate a colinear insertion product that can increase the size of the HMW DNA target. The target DNA can remain bumpable, and, thus, the target DNA can be separated from the transposasome reagent stream and unreacted adapter DNA. At 1010, HMW cointegrates can be purified from the transposase reagent stream. At 1012, cointegrates can be reacted with restriction enzyme to generate a sequencing library. At 1014, the library can be separated from uncut HMW DNA and recovered from the bump array. In some implementations, the final sequencing library can be cleaved from the HMW co-integrate DNA by bumping the DNA through a restriction enzyme reagent stream. The enzyme can cleave engineered sites in the modified transposon that lie just outside of the sequencing adapters. The cleaved library can be low in molecular weight (~200-2000 bp), and can be no longer bumpable. The library can be removed from the array in the restriction enzyme stream. Uncleaved, unreacted HMW DNA can be bumped out of the reagent stream diagonally (and can be recovered).

In some implementations, the current subject matter system can include micron-sized post arrays with high structural rigidity and high aspect ratios for the purposes of processing fluid samples. The bump arrays can be manufactured from silicon, cyclic olefin resin, molded plastic disposable flow cells, as well as any other materials.

In some implementations, bump arrays and systems can separate or fractionate, analyze, and/or collect purified or processed polynucleic acid analytes or fractions derived from a raw biological sample.

In some implementations, the current subject matter can also process smaller nucleic acid molecules by attaching the nucleic acids to microparticles that can be bumped in a bump array. The microparticles can act as carriers for transporting the attached nucleic acids through reagent streams for modification of the nucleic acids. For example, emulsion PCR with primer-modified microparticles can be used for generation of DNA sequencing template beads (Ion Torrent and 454 sequencing methods; Rothberg et al. 2011. Nature v475, pp 348-352; Margulies et al., Nature. V437, pp 376-380). In some implementations, emulsion PCR methods can be used for evaluation of the frequency of rare mutant genes in tissue from cancer patients (Vogelstein's "BEAMing" method, Diehl et al. Nature Methods. 2006 v3 pp 551-559). In some implementations, the current subject matter can be used to process particle-based emulsion PCR by combining washing, denaturation, and primer hybridization into a single bump array process. For example, a bump array can be designed with post spacing chosen so that the critical diameter of the array can be less than that of the microparticles used for the emulsion PCR. This can ensure that the microparticles can be bumped consistently at all positions within the array. After emulsion PCR, the emulsion is broken and the aqueous particles fraction is fed into the array near the upper left hand corner. As the particles enter the array, they can be bumped rightward, while the PCR reagents can flow downward in the direction of bulk flow (the directional flow can be similar to the one shown in FIGS. 5-7, for example). A suitable wash buffer can be fed into the top of the array immediately to the right of the particle input port. As the particles are bumped out of the input stream, they can pass through the wash buffer stream, which can clean away additional PCR reagent. As the particles move further down the array, they can enter a denaturing reagent stream (e.g., which can contain about 20-200 mM KOH or NaOH with about 1-10 mM EDTA), which can convert the double-stranded amplicons on the particles to single-stranded form. The non-covalently bound amplicon strand can be washed down the array with the denaturant stream, and the particles can be bumped rightward into a neutralizing buffer that can be suitable for hybridization reactions in the next step. Generally, such neutralizing buffer can contain a buffer (for example, 20-200 mM Tris-HCl, pH 7.5-8.0) and monovalent ions to support hybridization (for example, 20-500 mM NaCl). The particles can then be bumped through a hybridization reagent stream containing sequencing primer (in the case of the 454/Ion Torrent applications), or labeled oligonucleotide probe (in the case of the BEAMing application). The reagent stream can have oligo probes in the low micromolar concentration range (about 0.1 micromolar to about 50 micromolar), and can have about the same ionic strength as the neutralizing buffer stream described above. The ionic strength can be adjusted higher or lower as needed to achieve the correct stringency of hybridization. In the final processing step of the array, the hybridized particles are bumped out of the hybridization stream into a final wash buffer stream. This final wash buffer is chosen according to the downstream application to be used (sequencing in the case of 454/Ion applications, fluorescent particle sorting in the case of the BEAMing assay). The hybridized, washed particles are collected from the output port of the final wash buffer located near the lower right corner of the array.

EXAMPLES

Example 1

Bump Array Process for Purification of Leukocyte Nuclei from Whole Blood

A single array performs operations 1002 and 1004, shown in FIG. 10, encompassing separation of cells from plasma and isolation of leukocyte nuclei, respectively (as shown in FIG. 5). The array, shown schematically in FIG. 5, is designed to bump all particles >3-4 µm in diameter. Setting the critical dimension at this size bumps cells (red blood cells (RBCs) 6-8 µm, white blood cells (WBCs), 6-16 µm) and nuclei (5-9 µm) diagonally across the flow direction. Blood flows into a region of the array filled with buffered saline. As the cells bump through this region, they are washed free of plasma. Continuing laterally across the array, the cells are bumped into a stream of lysis buffer containing a concentration of non-ionic detergent sufficient to lyse RBCs and WBCs, but not WBC nuclei. Since the nuclei are still larger than the critical diameter of the array (3-4 mm), they follow the same diagonal path as the cells. The nuclei exiting the lysis buffer pass into a stream of wash buffer (lysis buffer without detergent, and are collected in an output reservoir near the bottom right corner of the array.

The post spacing of this array is based on a simplified version of the cell sorting array ("FD" device) of Davis et al., 2006. Proc Natl Acad Sci USA. v103, pp 14779-84, incorporated herein by reference in its entirety. That device utilized a constant post diameter (22 µm) and constant gap size ("G" in FIG. 1, 10 µm), but varied the row offset distance ("d" in FIG. 1) in stepwise fashion from small to large values. The smallest offset distance used in the Davis array, approximately 0.5 µm, gives a critical particle diameter for bumping of ~3 µm. This design is appropriate for this nuclear isolation array of this system, because the smallest diameter expected for nuclei (and cells) is ~5 µm. For these reasons, this system may use a constant offset of 0.5 µm throughout the array.

The overall dimensions of the array are also derived from the Davis sorting array, since the throughput of that array is a good match for DNA sequencing applications. The processing speed of that device was 1 µl of whole blood per hour. This corresponds to about 66 ng of genomic DNA per hour ($10^4$ WBC/µl×0.0066 ng DNA/cell). Standard DNA input recommendations for NGS library protocols have been decreasing steadily, and some practitioners can reproducibly produce libraries with 50-100 ng genomic DNA.

The concentration and type of detergent can be adjusted as needed to optimize nuclear yield. The relative array areas devoted to the various chip inputs will be investigated to optimize nuclear yield and purity. For instance, the width of the lysis buffer stream can be adjusted to alter the residency time of cells or nuclei in the lysis reagent. Similarly, the width of the wash buffer stream can be widened to provide a more stringent removal of detergent or lysed blood components from the nuclei. To facilitate investigation of these issues, early chip prototypes will be equipped with many regularly spaced input reservoirs. In such prototypes, the width of any reagent stream can be widened by filling additional adjacent input reservoirs with the reagent.

Example 2

Bump Array Process for Purification of HMW DNA from Isolated Leukocyte Nuclei The next process is purification of DNA from the cell nuclei. The system accomplishes this task using chaotropic salt solutions (4 M guanidine thiocyanate, GuSCN) to lyse nuclei and dissociate chromosomal proteins from the DNA. Lysis with chaotropes is faster and more complete than popular SDS-proteinase K protocols. Silicon arrays are chemically coated with fluorosilane to prevent DNA binding to the silicon oxide surfaces in the presence of high concentrations of chaotrope.

A pair of bump arrays with different post geometries is used for this process (as shown in FIG. 6). The first array has a geometry appropriate for bumping nuclei (critical particle diameter=~3-4 µm). In this region, the input stream of nuclei is passed into the GuSCN stream where the nuclei are lysed. DNA and dissociated nuclear proteins are smaller than the critical particle diameter, and flow with the lysis reagent. Large particles (>3-4 µm) such as partially unlysed nuclei, are bumped rightward and are trapped in a particle trap at the right edge of the device. This trap is a serpentine fluidic channel with many entry points running the length of the array. Unwanted particles enter the trap channel and remain there slowly traversing the long channel for the duration of the DNA purification process. The lysis stream carrying the DNA and denatured protein is piped into the input port of the second array. The second array has a critical particle diameter of around 0.6 µm, which bumps double-stranded linear molecules >~40 kb. As a result, HMW DNA is bumped out of the GuSCN stream, and is washed in a buffer stream as it travels rightward to the collection reservoir at the lower right corner.

A key issue for this process is how the nuclei behave as they begin to lyse. There is a risk that extremely large, chromosome-sized DNA molecules (>200 kb), that may spill out of partially lysed nuclei, could become entangled with the array posts and/or other nuclei, and clog the array. A related issue is whether such extremely large DNA molecules can clog the arrays, even in purified form. To overcome these issues, the average size of the nuclear DNA can be reduced before lysis, by, for example, treating the nuclei with a low concentration of either a nuclease or a chemical cleavage agent. Preferably, the average DNA size is reduced to between 50 and 200 kb, where bump array technology works well. Preferred reagents would be double-strand endonucleases like micrococcal nuclease or rare-cutting restriction enzymes. Optionally, the cleavage reagent stream is positioned immediately to the right of the nuclear sample input in the first array (left of the GuSCN input stream), so that the cleavage agent is washed in and out of the nuclei before entering the lysis stream. Alternatively, a cleavage process step is inserted into the array of Example 1 (which illustrates operation 1002 shown in FIG. 10).

Another important parameter in this process is the time of exposure to the GuSCN reagent needed to obtain efficient lysis. The width of the GuSCN layer, the bump angle of the array (adjustable by changing gap and offset of the array), and the flow rate are critical variables that are manipulated to vary exposure time. The lysis process is monitored in real time using microscopy of nuclei passing through the arrays. DNA recovery and purity are measured using standard DNA and protein assays.

Example 3

Bump Array Process for NGS Library Formation

Purified HMW genomic DNA from the arrays of Example 2 (which illustrates operations 1006 and 1008 shown in FIG. 10) is passed to an array that performs a transposition-mediated library formation reaction (as shown in FIG. 7). The array geometry of the library array is similar to that of the second array of Example 2 (which illustrates operation 1008 shown in FIG. 10): DNA bigger than ~40 kb is bumped rightward into a tranposase-based library formation reagent stream (as shown in FIG. 7).

This library formation reaction is a modification of the Nextera library concept (Epicentre Biotechnologies/Illumina). In contrast to the Nextera system, this system uses recombinant transposon substrates carrying both transposon ends on the same linear double-stranded DNA (dsDNA) molecule (as shown in FIGS. 8A-B). The transposition reaction inserts the entire recombinant transposon into the HMW genomic target DNA. The critical feature of this reaction is that the co-integrate product remains high in molecular weight, and, therefore, the bump array process can be used to purify the reaction products away from free transposase and unreacted transposon substrates.

After bumping out (i.e., removing) of the transposase reagent stream, the co-integrate DNA is washed in a buffer stream, and bumped into a restriction enzyme reagent stream. The restriction enzyme cleaves just outside of the NGS adapter sequences on the 5' sides of the transposon ends (as shown FIGS. 8A-B). The final library is low in molecular weight (fragments ranging ~200-2000 bp), and is recovered from the array in the restriction enzyme stream. Additional purification of the library can be performed to remove the restriction enzyme prior to loading the library on the sequencer.

Transposase enzymes suitable for NGS library construction are commercially available (Nextera, a mutant Tn5 transposase). Epicentre also sells linear Tn5 transposon substrates for insertional mutagenesis and Sanger sequencing (see EZ-Tn5™<oriV/KAN-2> Transposon Insertion Kit). These linear substrates are used for initial testing of the proposed bump array process. For instance, the Tn5-KAN-2 commercial substrate can be inserted into a defined HMW target such as phage lambda DNA. Transposition efficiency is assessed by electrophoresis, restriction mapping (the transposon and lambda each have single sites for the enzyme Xho I), or blot hybridization of the product DNA.

For commercialization, recombinant transposon substrates with Tn5 ends, NGS adapter sequences, and rare-cutting restriction sites for library release are constructed using standard recombinant DNA methods. Alternatively, other high activity in vitro transposition systems, such as Tn552 from *S. aureus* may be used.

Operation 1014 shown in FIG. 10 can optimize the two enzymatic library construction reactions for efficient utilization of genomic DNA (and reagents). As mentioned previously, reagent concentration, bump angle, reagent stream width, post array spacing, and flow rate can all be adjusted to optimize the reagent-DNA contact time.

Example 4

Bump Array Process for Isolation of Bacterial DNA from a Human Blood Sample

Step 1.
A sample of human blood is treated with non-ionic detergent under conditions where RBCs and WBCs are lysed, but WBC nuclei remain intact (0.32 M sucrose, 5 mM MgCl2, 1% Triton X-100, 0.01 M Tris-HCl, pH 7.6). These conditions are not strong enough to lyse bacteria, and they remain in the lysate as intact cellular forms.

Step 2.
The lysate is fed into a first post array designed to bump particles 3-4 microns in diameter. The post array of Example 1 has suitable spacing for this application. The lysate is fed into the array near the left top corner. Large particles including WBC nuclei and partially lysed human cells are bumped rightward, while smaller particles, including bacterial cells, travel in the same direction at the bulk fluid flow, straight down the left side of the array, and are recovered from the bottom left side of the array.

Step 3.
The small particle output of the first array (from left side), is fed into a second post array that is designed to bump bacterial cells (critical diameter for bumping approximately 0.7 microns). Design of such arrays is described in Morton et al., 2008 (Morton K J, Loutherback K, Inglis D W, Tsui O K, Sturm J C, Chou S Y, Austin R H. 2008. Lab Chip. v8, pp 1448-1453, incorporate herein by reference in its entirety). The small particle lysate from the first array is fed into the array near top left corner. The second array is designed to have three separate reagent streams entering the array on the right side of the lysate input port. The four input ports for sample and reagents (reagent streams 1-3) are separated by wash buffer ports, so that low molecular weight compounds are washed from the bumped components before entering the next reagent stream.

Step 4.
As the lysate flows into the second post array, bacterial cells are bumped rightward from the lysate stream into isotonic wash buffer (50 mM Tris-HCl, pH 8.0, 150 mM NaCl, 1.125 M sucrose; Morton et al., 2008). As the bacterial cells flow further down the array, they are bumped rightward into the first reagent stream, which contains enzymes that degrade bacterial cell walls (hen egg white lysozyme, mutanolysin) and detergents to lyse the bacterial membrane in isotonic wash buffer (0.4 mg/ml lysozyme and mutanolysin, 8% weight/volume sucrose, 10 mM EDTA, 1 M NaCl, 0.5% Brij 58, 0.2% deoxycholate). Bacterial cells-will be lysed in this reagent stream, but the bacterial chromosome will remain in a compacted, bumpable form, known as a nucleoid (Worcel A, Burgi E. 1972. J. Mol. Biol. v71, pp 127-147, incorporated herein by reference in its entirety). As the nucleoids flow further into the array, they are bumped into a buffer stream which removes components of the first reagent stream and conditions the nucleoids for the next reagent stream (50 mM Tris HCl, 150 mM NaCl, pH 7.9).

Step 5.
The nucleoids are bumped into a second reagent stream which contains a restriction enzyme with a rare sequence specificity (such as the enzymes Not I or Sfi I, both available from New England Biolabs), in a buffer that will support enzyme activity (for Not I, conditions are 50 mM Tris HCl, 150 mM NaCl, 10 mM MgCl2, pH 7.9, 100 micrograms/ml bovine serum albumin, 1 mM dithiothreitol). This treatment cleaves the bacterial chromosome into fragments ranging in size between 40 kb and 1000 kb (Smith C L, Econome J G, Schutt A, Klco S, Cantor C R. 1987. Science. v236, pp 1448-1453, incorporated herein by reference in its entirety), but will leave the nucleoids in compacted form and associated with packaging proteins. The purpose of the restriction cleavage is to reduce the average DNA fragment size in the nucleoids so that the chromosomal DNA will not clog the array in the next step, in which the packaging proteins are stripped from the DNA. As the still-folded nucleoids flow down the array they are bumped out of the second reagent stream into a wash buffer without enzymes (50 mM Tris HCl, pH 7.9, 150 mM NaCl).

Step 6.

The nucleoids are bumped into a third reagent stream containing a high concentration of chaotrope (4 M guanidine isothiocyanate). This treatment completely dissociates the nucleoids into free protein and DNA. The majority of the bacterial DNA will be in fragments that are greater than 40 kb. Linear DNA molecules of this size will behave as particles with a diameter of around 1 micron (Robertson R M, Laib S, Smith D E. 2006. Proceedings of the National Acad USA. v103, pp 7310-7314, incorporated herein by reference in its entirety), and therefore they will bump in the array to the right, just as the bacterial cells and nucleoid did. The associated nucleoid proteins are too small to be bumped by the array and will travel straight down the array with the chaotrope reagent stream. The DNA is bumped rightward out of the chaotrope reagent stream and into a final buffer suitable for DNA storage, or alternatively, a buffer suitable for the next processing steps, as appropriate. The purified final DNA products are collected from channels exiting the array near the lower right corner.

Step 7.

Optionally, the purified DNA from Step 6 can be fed into an array as described in Example 1 for generation of DNA sequencing libraries. The sequence information obtained can be used to diagnose infections, and also guide treatment decisions by revealing drug resistances and sensitivities of the infecting organism.

In some implementations, the current subject matter can be implemented together with the use of various computing systems and/or computer program products. Such systems and products can be used to process, monitor, collect, and/or otherwise assist the various components of the current subject matter's system. Such computer program products can comprise non-transitory computer readable media storing instructions, which when executed one or more data processor of one or more computing systems, causes at least one data processor to perform operations herein. Similarly, such computer systems can include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems.

The computing systems and/or products that can be used in conjunction with the systems and methods disclosed herein can be embodied in various forms including, for example, a data processor, such as a computer that also includes a database, digital electronic circuitry, firmware, software, or in combinations of them. Moreover, the above-noted features and other aspects and principles of the present disclosed implementations can be implemented in various environments. Such environments and related applications can be specially constructed for performing the various processes and operations according to the disclosed implementations or they can include a general-purpose computer or computing platform selectively activated or reconfigured by code to provide the necessary functionality. The processes disclosed herein are not inherently related to any particular computer, network, architecture, environment, or other apparatus, and can be implemented by a suitable combination of hardware, software, and/or firmware. For example, various general-purpose machines can be used with programs written in accordance with teachings of the disclosed implementations, or it can be more convenient to construct a specialized apparatus or system to perform the required methods and techniques.

The systems and methods disclosed herein can be implemented as a computer program product, i.e., a computer program tangibly embodied in an information carrier, e.g., in a machine readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

As used herein, the term "user" can refer to any entity including a person or a computer.

Although ordinal numbers such as first, second, and the like can, in some situations, relate to an order; as used in this document ordinal numbers do not necessarily imply an order. For example, ordinal numbers can be merely used to distinguish one item from another. For example, to distinguish a first event from a second event, but need not imply any chronological ordering or a fixed reference system (such that a first event in one paragraph of the description can be different from a first event in another paragraph of the description).

The foregoing description is intended to illustrate but not to limit the scope of the embodiments of the disclosure, which is defined by the scope of the appended claims. Other implementations are within the scope of the following claims.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user can provide input to the computer. Other kinds of devices can be used to provide for interaction with a user as well. For example, feedback provided to the user can be any form of sensory feedback, such as for example visual feedback, auditory feedback, or tactile feedback; and input from the user can be received in any form, including, but not limited to, acoustic, speech, or tactile input.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the flows depicted in the accompanying figures and/or described herein do not necessarily require the particular order shown, or sequential order, to achieve desirable results. Other implementations can be within the scope of the following claims.

Example embodiments of the methods and components of the present disclosure have been described herein. As noted elsewhere, these example embodiments have been described for illustrative purposes only, and are not limiting. Other embodiments are possible and are covered by the present disclosure. Such embodiments will be apparent to persons skilled in the relevant art(s) based on the teachings contained herein. Thus, the breadth and scope of the present disclosure should not be limited by any of the above-described exemplary embodiments, but should be defined only in accordance with the following claims and their equivalents.

What is claimed:

1. A system for processing of a biological fluid, comprising:
    at least one input reservoir for receiving a biological fluid and separating one or more cells therefrom;
    at least one bump array mechanism configured with a plurality of treatment areas including at least:
        a first treatment area configured with a first buffer, and
        a second treatment area configured with a transposase complex having at least one sequencing adaptor; and
    at least one output reservoir, wherein
        the first treatment area is configured to generate a purified deoxyribonucleic acid ("DNA") from the one or more cells upon the one or more cells traversing the first treatment area,
        the second treatment area is configured to receive the purified DNA and combine the purified DNA with a transposase complex having at least one sequencing adaptor to produce a second solution, and
        the at least one output reservoir is configured to receive at least the second solution.

2. The system according to claim 1, wherein the biological fluid includes at least one of the following: whole blood, urine, spinal fluid, saliva, buccal swabs, sputum, bronchial lavage, gastric lavage fluid, microbial culture media, feces, buffy coat, serum, plasma, platelet concentrate, water samples, and/or any other biological, chemical, and/or biochemical fluids and/or any combination thereof.

3. The system according to claim 1, wherein the at least one bump array uses a deterministic lateral displacement to process at least one of the purified DNA and the second solution.

4. The system according to claim 1, further comprising a sequential arrangement of a plurality of bump arrays to process at least one of the purified DNA and the second solution.

5. The system according to claim 1, wherein the biological fluid is whole blood.

6. The system according to claim 1, wherein the at least one output reservoir fractionates the output solutions based on a size of at least one cell contained within the output solution.

7. The system of claim 1, wherein the at least one input reservoir comprises a plurality of input reservoirs.

8. The system of claim 7, wherein the plurality of input reservoirs comprise a first reservoir having at least the biological fluid, a second reservoir having the first buffer, and a third reservoir having the transposase complex having the at least one sequencing adaptor.

9. The system of claim 8, further comprising a plurality of input ports configured to direct the contents of respective reservoirs into the at least one bump array.

10. The system of claim 1, further comprising a particle trap.

11. The system of claim 10, wherein the at least one bump array is configured with the particle trap.

12. The system of claim 1, wherein the first buffer comprises a cell lysis buffer.

13. The system of claim 1, wherein the plurality of treatment areas further comprise at least one of: a third treatment area configured with a wash buffer and a fourth treatment area configured with a guanidine isothiocyanate (GuSCN) buffer.

14. The system of claim 13, wherein the wash buffer comprises a nuclear wash buffer.

15. The system of claim 13, wherein the GuSCN buffer is configured to dissociate nuclei and remove nuclear proteins from DNA.

* * * * *